US00PP34883P2

(12) United States Plant Patent
Halladin

(10) Patent No.: US PP34,883 P2
(45) Date of Patent: Jan. 3, 2023

(54) ***PICEA PUNGENS* TREE NAMED 'INMOHOOP'**

(50) Latin Name: *Picea pungens*
Varietal Denomination: INMoHoop

(71) Applicant: Early Morning LLC, Boring, OR (US)

(72) Inventor: Paul H. Halladin, Boring, OR (US)

(73) Assignee: EARLY MORNING LLC, Boring, OR (US)

( * ) Notice: Subject to any disclaimer, the term of this patent is extended or adjusted under 35 U.S.C. 154(b) by 0 days.

(21) Appl. No.: 17/875,954

(22) Filed: Jul. 28, 2022

(51) Int. Cl.
*A01H 7/00* (2006.01)

(52) U.S. Cl.
USPC ..... Plt./213

(58) Field of Classification Search
USPC ..... Plt./213
CPC ..... A01H 7/00; A01H 5/00
See application file for complete search history.

(56) References Cited

U.S. PATENT DOCUMENTS

PP5,457 P * 4/1985 Holden ..... Plt./213

* cited by examiner

*Primary Examiner* — June Hwu
(74) *Attorney, Agent, or Firm* — Weatherly IP Solutions, LLC; Barbara Campbell

(57) ABSTRACT

A new and distinct variety of *Picea pungens* tree having an orthotropic leader growth, a dwarf and wide conical shape, a compact habit, blue-colored needles/foliage, and long and thin needles, as disclosed.

3 Drawing Sheets

Genus and species: *Picea pungens.*
Denomination: 'INMoHoop'.

BACKGROUND

'INMoHoop' is a new and distinct variety of *Picea pungens*. 'INMoHoop' originated from a controlled cross conducted in May 2001 in a greenhouse in Boring, Oreg. of the female *Picea pungens* parent 'Montgomery'(unpatented) and the female *Picea pungens* parent 'Hoopsi' (unpatented). The seeds from this cross germinated in May 2002.

'INMOHOOP' was selected and first asexually propagated in January 2009 in Boring, Oreg. via grafting onto *Picea abies* rootstock (unpatented).

'INMoHoop' reproduces true to type in successive generations since 2009 of asexual reproduction via grafting onto *Picea abies* rootstock (unpatented).

SUMMARY

The following are the most outstanding and distinguishing characteristics of this new variety when grown under normal horticultural practices in Boring, Oreg.

1. Orthotropic leader growth;
2. Dwarf and wide conical shape;
3. Compact habit;
4. Blue-colored needles/foliage; and
5. Long and thin needles.

DESCRIPTION OF THE PHOTOGRAPHS

This new *Picea pungens* tree is illustrated by the accompanying photographs which show the plant's overall plant habit including form and foliage. The photographs are of a 10-year-old tree grown outdoors in Boring, Oreg. and were taken in June 2022 under cloudy conditions. The colors shown are as true as can be reasonably obtained by conventional photographic procedures.

DETAILED DESCRIPTION

Figure 1:
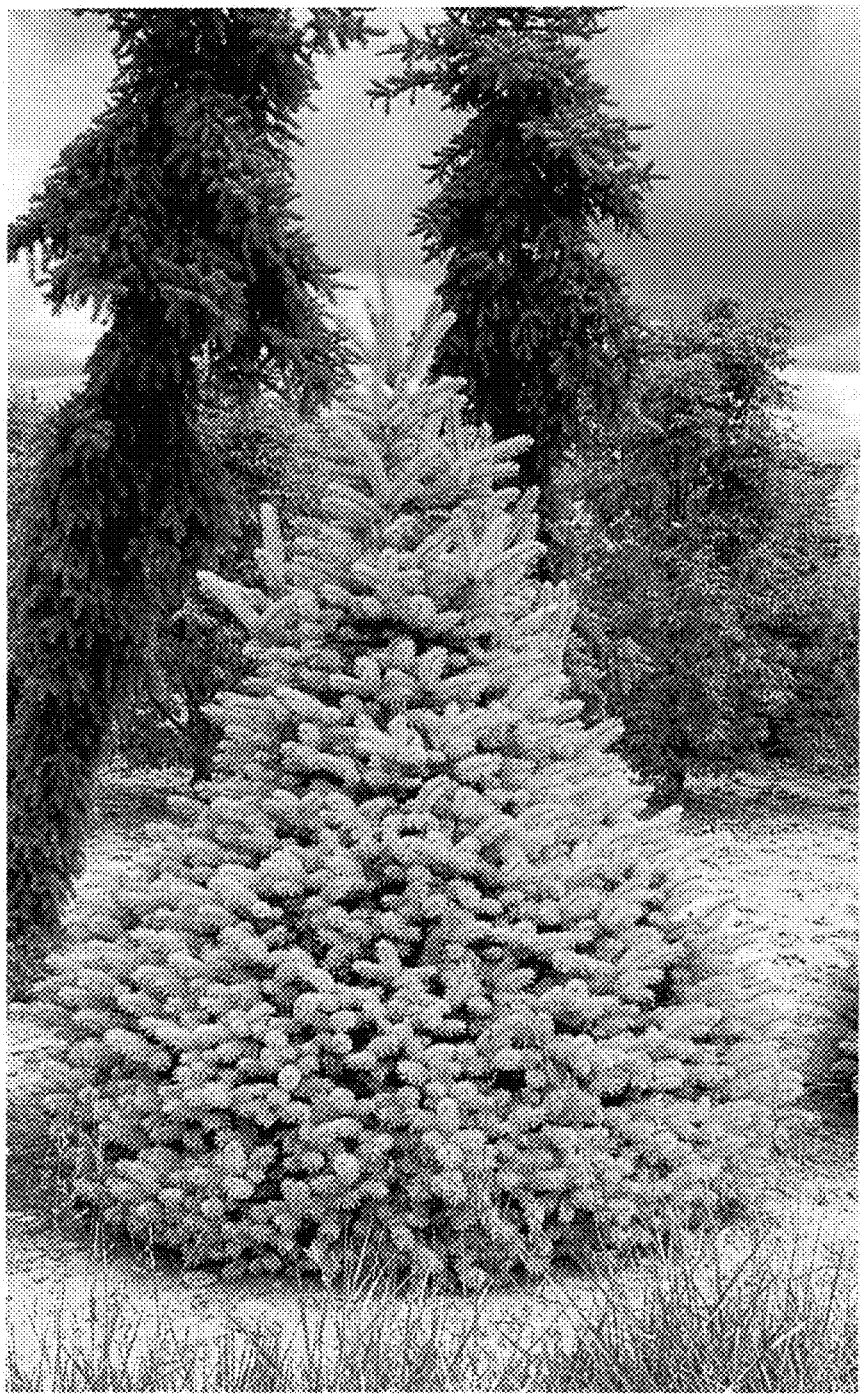
FIG. 1 shows the overall form of the whole tree of 'INMoHoop'.
Figure 2:
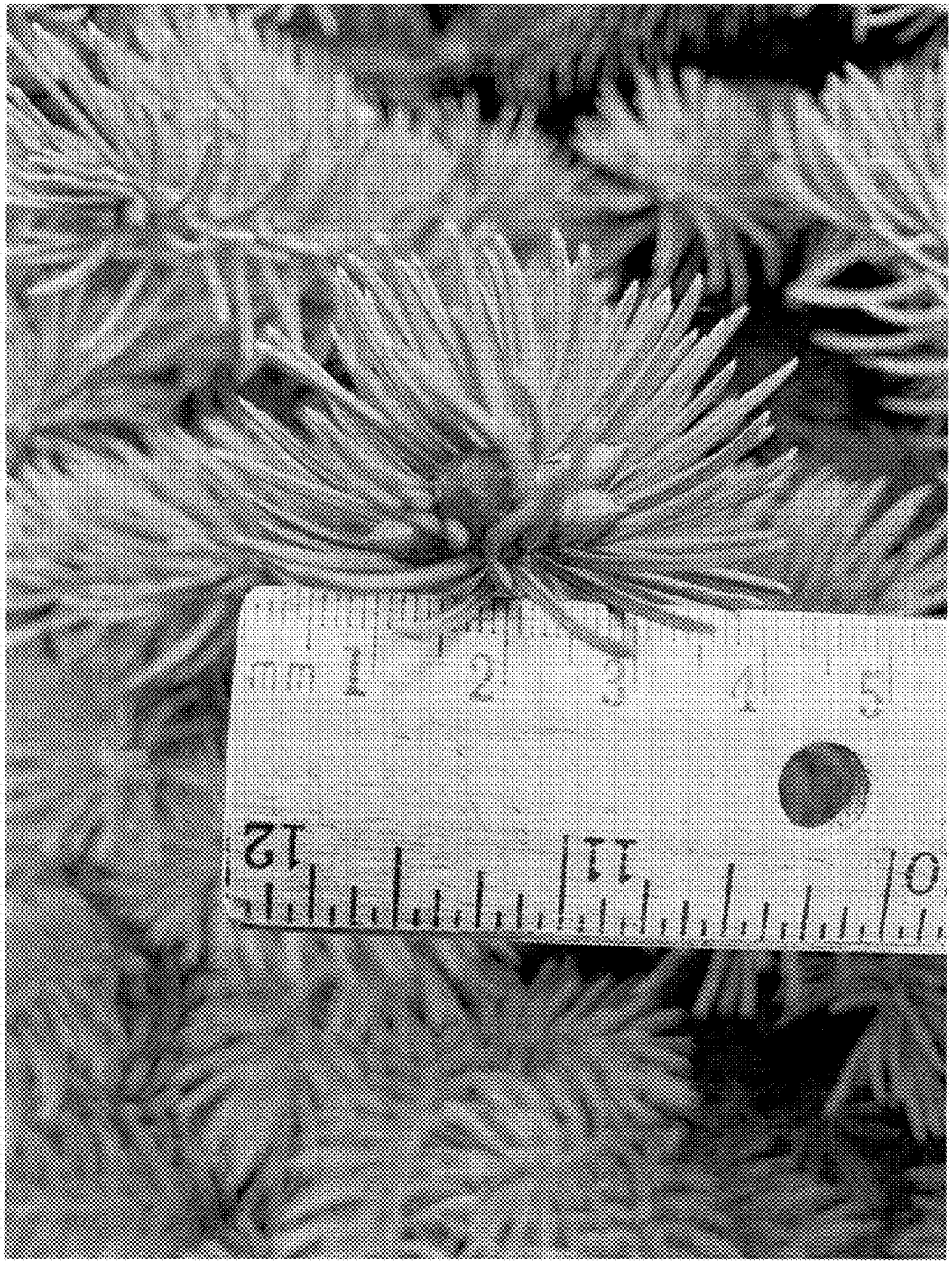
FIG. 2 shows a close-up of the buds and needles or leaves of the tree of FIG. 1.
Figure 3:
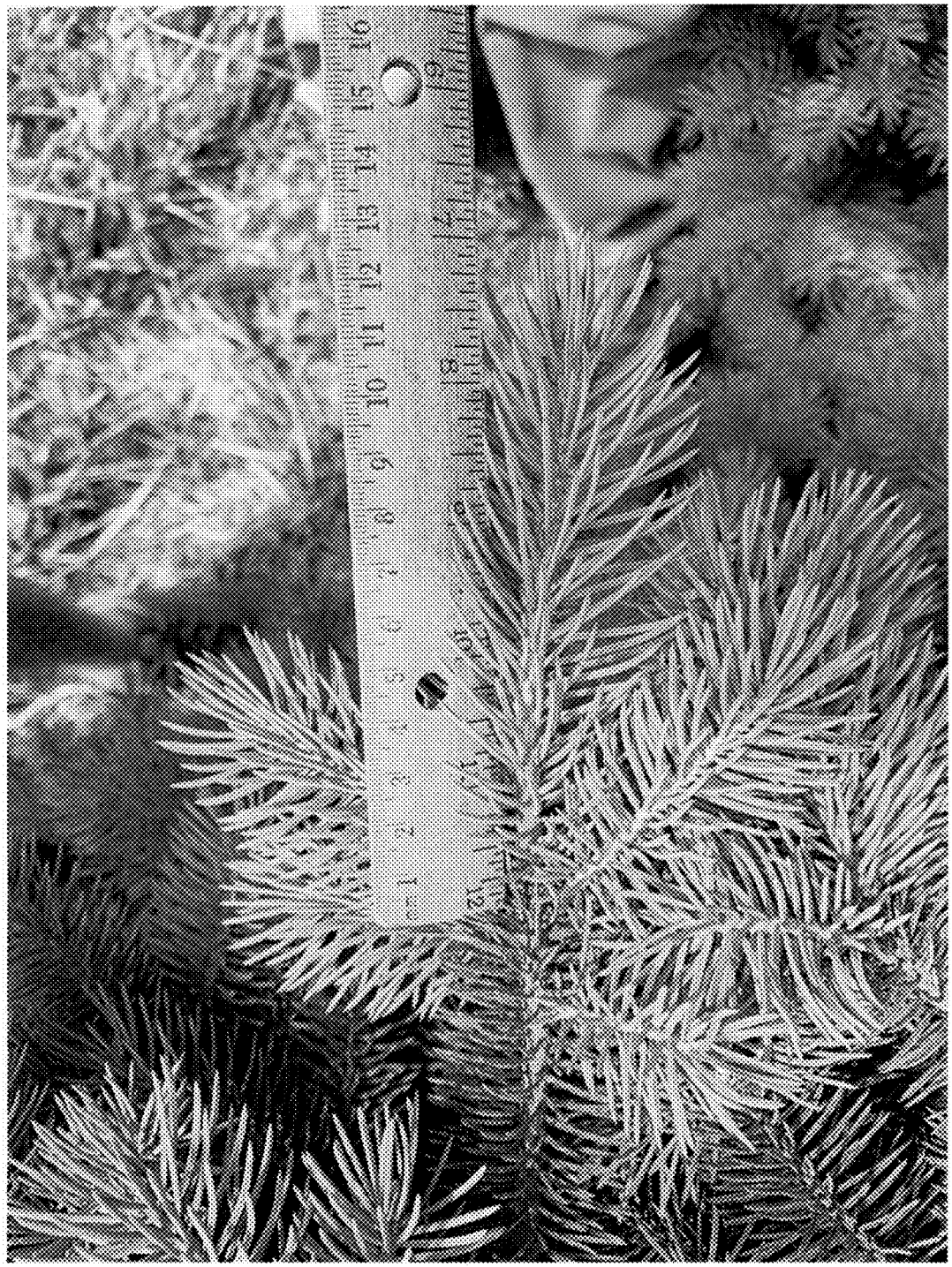
FIG. 3 shows a close-up of the terminal branch shoot of the tree of FIG. 1.

The following detailed descriptions set for the distinctive characteristics of 'INMoHoop'. The data which define these characteristics were collected outdoors in Boring, Oreg. in June 2022 on 10-year-old trees in Boring, Oreg. Color references are to The R.H.S. Colour Chart of The Royal Horticultural Society of London (R.H.S.) 2001, except where general terms of ordinary dictionary significance are used.

Classification:
- *Family.*—Pinaceae.
- *Botanical.—Picea pungens.*
- *Denomination.*—'INMoHoop'.

Tree:
- *Type.*—Evergreen conifer.
- *Shape.*—Wide conical.
- *Growth and branching habit.*—Dwarf compact tree, single flush.
- *Propagation type.*—Grafting onto *Picea abies* rootstock (unpatented).
- *Height (from soil line).*—150 cm at 10 years.
- *Width (horizontal plant diameter).*—120 cm at 10 years.
- *Length of terminal 1-year shoots.*—20.0 cm to 30.0 cm.

*Length of subterminal* 1-*year shoots*.—10.0 cm to 15.0 cm.

*Diameter of trunk*.—10.0 cm at 10 years at a height of 30.0 cm on the trunk.

*Temperature tolerance or zones*.—USDA Zones 2 to 8.

*Trunk surface texture*.—Surface has irregular, small, and rough scaly plates.

*Trunk color*.—RHS N199D (Greyed-Brown) and RHS N167D (Greyed-Orange).

*Lateral branch color for* 1-*year-old shoot*.—RHS 166D (Greyed-Orange).

Leaves (needles):

*Arrangement*.—Radial, single.

*Quantity of leaves/needles per terminal one-year branch shoot*.—450 to 475.

*Quantity of leaves/needles per subterminal one-year branch shoot*.—200 to 250.

*Shape*.—Needle-like, acicular.

*Apex*.—Acute.

*Base*.—Attenuate, attached to leaf peg.

*Margin*.—Entire, smooth.

*Leaf length, terminal shoot*.—Basal: 1.5 cm to 2.0 cm; Medial: 3.0 cm to 3.5 cm.

*Distal*.—2.0 cm to 2.5 cm.

*Width*.—0.1 cm.

*Texture*.—Smooth and covered with waxy layer.

*Pubescence*.—Absent.

*Curvature of the needles*.—On the apical needles, there is no curvature (the needles are straight); on the terminal leaf branch shoot, the upper shoot needles have a very slight forward curvature and the needles on the side and lowers are straight (no curvature); on the small, lateral shoots, the curvature of the needles is absent to very slight.

*Immature leaf color*.—RHS 122D (Blue-Green).

*Mature leaf color for both upper and lower surfaces*.—RHS 122D (Blue-Green).

*Mature leaf color when wax rubbed off*.—RHS 189A (Greyed-Green).

*Petioles*.—Leaves are sessile on a short peg.

Buds:

*Shape*.—Conical with a pointed apex.

*Color*.—RHS 165C (Greyed-Orange).

*Size*.—2.0 cm height and 1.0 cm width at the leader branches and 1.2 cm height, 0.5 cm width at the terminal branches and 0.5 cm height and 0.3 cm width on the small secondary shoots.

*Scales*.—Present, smooth and papery and adhering to the bud shape when wet or newly developed; when dry or mature, the papery bud scales are reflexed from the tip.

*Terminal bud burst*.—Within the months of April and May.

Cones: No male or female cones have been observed to date.

Disease/pest resistance: No specific disease or pest resistance has been observed to date.

COMPARISON WITH PARENTAL AND COMMERCIAL LINES

Table 1 shows a comparison of the differences between 'INMoHoop' and the commercial *Picea pungens* tree 'Fat Albert' (unpatented).

TABLE 1

Comparison with Commercial Line

| Characteristic | 'INMoHoop' | 'Fat Albert' |
|---|---|---|
| Growth habit | Dwarf compact tree | Large open tree |
| Size, height × width at 10-years-old | 150 cm × 120 cm | 290 cm × 190 cm |
| Mature needle/leaf color | RHS 122D (Blue-Green) | RHS 130D (Green) |

Table 2 shows a comparison of differences between 'INMoHoop' and the parental lines.

TABLE 2

Comparison with Parental Lines

| Characteristic | 'INMoHoop' | Male parent 'Hoopsi' | Female parent 'Montgomery' |
|---|---|---|---|
| Shape | Wide conical as both an immature and mature tree | Irregular conical | Irregular flattened mound as an immature tree and wide conical as a mature tree |
| Branch growth type | Orthotropic | Plagiotropic | Plagiotropic |
| Growth habit | Dwarf and compact | Large open tree; staking and pruning required for tree-like habit | Dwarf compact tree; flattened mound when immature and wide-conical when mature |
| Growth rate cm/year | 20 cm to 30 cm | 35 cm to 45 cm | 10 cm to 20 cm |
| Size, height × width at 10-years-old | 150 cm × 120 cm | 230 cm × 135 cm | 90 cm × 105 cm |
| Mature needle/leaf color | RHS 122D (Blue-Green) | RHS 112C (Blue-Green) | RHS 122B (Blue-Green) |
| Leaf./needle length, medial | 3.0 cm to 3.5 cm | 2.2 cm to 2.5 cm | 2.2 cm to 2.5 cm |
| Leaf/needle width | 0.1 cm | 0.2 cm | 0.1 cm |

I claim:

1. A new and distinct variety of *Picea pungens* tree designated 'INMoHoop' as illustrated and described herein.

* * * * *